United States Patent [19]

Maurer et al.

[11] 4,234,587
[45] Nov. 18, 1980

[54] COMBATING PESTS WITH N,N-DIMETHYL-CARBAMIC ACID O-(2-SUBSTITUTED-METHYL-PYRIMIDIN-4-YL)-ESTERS

[75] Inventors: Fritz Maurer; Rolf Schröder, both of Wuppertal; Ingeborg Hammann, Cologne; Bernhard Homeyer; Paul-Ernst Frohberger, both of Leverkusen, all of Fed. Rep. of Germany

[73] Assignee: Bayer Aktiengesellschaft, Leverkusen, Fed. Rep. of Germany

[21] Appl. No.: 68,795

[22] Filed: Aug. 22, 1979

[30] Foreign Application Priority Data

Sep. 2, 1978 [DE] Fed. Rep. of Germany ....... 2838359

[51] Int. Cl.³ ................. C07D 239/34; C07D 239/70; C07D 239/90
[52] U.S. Cl. ................................. 424/251; 544/253; 544/319
[58] Field of Search ................. 544/253, 319; 424/251

[56] References Cited

U.S. PATENT DOCUMENTS 2,694,712 11/1954 Gysin et al. ......................... 544/319
3,652,566 3/1972 Ghosh et al. ......................... 544/253

Primary Examiner—Donald G. Daus
Assistant Examiner—James H. Turnipseed
Attorney, Agent, or Firm—Sprung, Felfe, Horn, Lynch & Kramer

[57] ABSTRACT

N,N-Dimethyl-carbamic acid O-(2-substituted-methyl-pyrimidin-4-yl)-esters of the formula

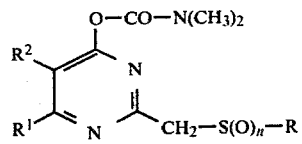

in which
R is alkyl,
$R^1$ is hydrogen or alkyl,
$R^2$ is hydrogen, alkyl or halogen, or
$R^1$ and $R^2$ together are alkanediyl, and
n is 1 or 2, which possess arthropodicidal and fungicidal properties.

10 Claims, No Drawings

COMBATING PESTS WITH N,N-DIMETHYL-CARBAMIC ACID O-(2-SUBSTITUTED-METHYL-PYRIMIDIN-4-YL)-ESTERS

The present invention relates to and has for its objects the provision of particular new N,N-dimethyl-carbamic acid O-(2-substituted-methyl-pyrimidin-4-yl)-esters which possess arthropodicidal and fungicidal properties, active compositions in the form of mixtures of such compounds with solid and liquid dispersible carrier vehicles, and methods for producing such compounds and for using such compounds in a new way especially for combating pests, e.g. insects, acarids and fungi, with other and further objects becoming apparent from a study of the within specification and accompanying examples.

It is known that certain N,N-dialkyl-carbamic acid O-pyrimidinyl esters, for example N,N-dimethyl-carbamic acid O-(2-isopropyl-6-methyl-pyrimidin-4-yl) and O-(2-methylthio-6-methyl-pyrimidin-4-yl) ester, have insecticidal properties (see French patent specification No. 1,443,910 and U.S. Pat. No. 2,694,712).

It is also known that certain dithiocarbamates, for example zinc ethylene-1,2-bis-(dithiocarbamate), are fungicidally active (see Phytopathology 33 (1943), 1,113).

However, the insecticidal and fungicidal activity of these compounds known from the state of the art is not always satisfactory, especially at low concentrations of active compound and when low amounts are used.

The present invention now provides, as new compounds, the N,N-dimethyl-carbamic acid O-pyrimidinyl esters of the general formula

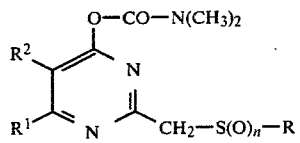

in which
R represents alkyl,
$R^1$ represents hydrogen or alkyl,
$R^2$ represents hydrogen, alkyl or halogen, or
$R^1$ and $R^2$ together represent alkanediyl, and
n represents 1 or 2.

Preferably, in formula (I), R represents straight-chain or branched alkyl with 1 to 5 carbon atoms, $R^1$ represents hydrogen or straight-chain or branched alkyl with 1 to 6 carbon atoms, $R^2$ represents hydrogen, straight-chain or branched alkyl with 1 to 6 carbon atoms, chlorine or bromine, or $R^1$ and $R^2$ together represent straight-chain α,ω-alkanediyl with 3 to 5 carbon atoms, and n represents 1 or 2.

Compounds of the formula (I) that are particularly preferred are those in which R represents straight-chain or branched alkyl with 1 to 3 carbon atoms, $R^1$ represents hydrogen or straight-chain or branched alkyl with 1 to 4 carbon atoms, $R^2$ represents hydrogen, straight-chain or branched alkyl with 1 to 4 carbon atoms, chlorine or bromine, or $R^1$ and $R^2$ together represent straight-chain α,ω-alkanediyl with 3 or 4 carbon atoms and n represents 1 or 2.

Surprisingly, the N,N-dimethyl carbamic acid O-pyrimidinyl esters according to the invention exhibit a considerably higher insecticidal action than the compounds of analogous structure and the same type of action which are known from the state of the art, and a considerably better fungicidal action than the known zinc ethylene-1,2-bis-(dithiocarbamate).

The invention also provides a process for the preparation of an N,N-dimethyl-carbamic acid O-pyrimidinyl ester of the formula (I) in which (a) a 4-hydroxy-pyrimidine of the general formula

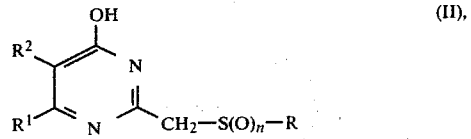

in which R, $R^1$, $R^2$ and n have the meanings stated above, is reacted with an N,N-dimethyl-carbamic acid halide of the general formula

in which
Hal represents chlorine or bromine,
if appropriate in the presence of an acid acceptor and if appropriate using a diluent, or (b) a 4-hydroxy-pyrimidine of the general formula (II) above, in which R, $R^1$, $R^2$ and n have the meanings stated above, is reacted with phosgene and the product is then reacted with dimethylamine, if appropriate in the presence of an acid acceptor and if appropriate using a diluent.

A compound of the formula (I) in which
R, $R^1$ and $R^2$ have the meanings stated above and n represents 1,
is also obtained by a process in which
(c) an N,N-dimethyl-carbamic acid O-pyrimidin-4-yl ester of the formula (I) in which
R, $R^1$ and $R^2$ have the meanings stated above and n represents zero,
is reacted with an equimolar amount of hydrogen peroxide, if appropriate using a diluent.

A compound of the formula (I) in which
R, $R^1$ and $R^2$ have the meanings stated above and n represents 2,
is also obtained by a process in which
(d) an N,N-dimethyl-carbamic acid O-pyrimidin-4-yl ester of the formula (I) in which
R, $R^1$ and $R^2$ have the meanings stated above and n represents zero,
is reacted with at least two molar equivalents of m-chloroperbenzoic acid, if appropriate in the presence of a diluent.

If the starting materials used are, for example, 2-ethylsulphonylmethyl-5,6-dimethyl-4-hydroxy-pyrimidine and N,N-dimethyl-carbamic acid chloride in process variant (a), 2-ethylsulphonylmethyl-5,6-dimethyl-4-hydroxy-pyrimidine, phosgene and dimethylamine in process variant (b), N,N-dimethyl-carbamic acid O-(2-n-propylthiomethyl-5-bromo-6-methyl-pyrimidin-4-yl) ester and hydrogen peroxide in process variant (c) and N,N-dimethyl-carbamic acid O-(2-methyl-thiomethyl-5-methyl-6-ethyl-pyrimidin-4-yl) ester and m-chloroperbenzoic acid in process variant (d), the corresponding reactions can be outlined by the following equations:

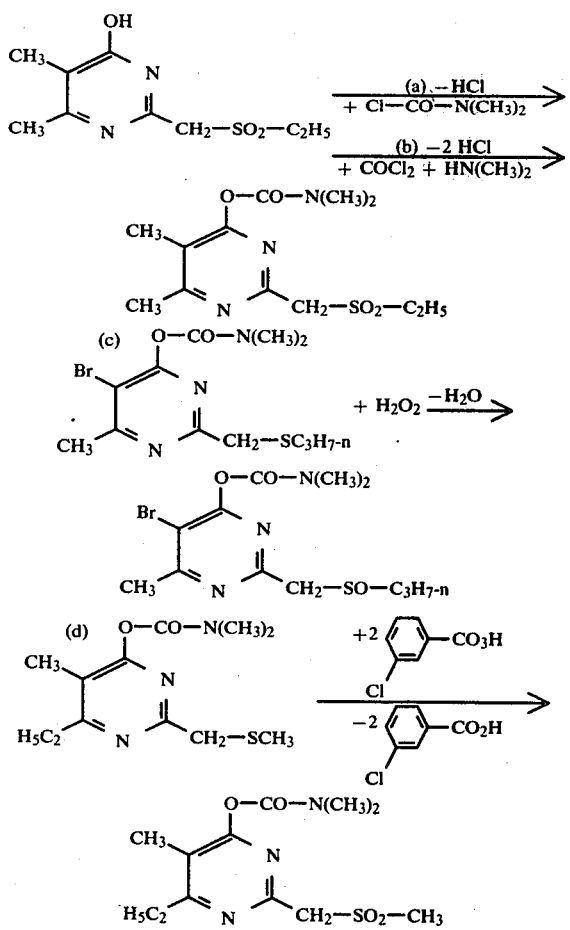

Formula (II) provides a definition of the 4-hydroxy-pyrimidines to be used as starting materials in process variants (a) and (b). Preferably, in this formula, R, $R^1$ and $R^2$ have those meanings which have been mentioned as preferred in the case of the definition of R, $R^1$ and $R^2$ in formula (I), and n represents 1 or 2.

The 4-hydroxy-pyrimidines of the formula (II) are obtained, for example, by reacting the corresponding 2-chloromethyl-4-hydroxy-pyrimidines with sodium mercaptides at temperatures between 20° and 100° C., if appropriate using a diluent, for example acetonitrile, filtering the mixture, stripping off the diluent from the filtrate and reacting the 2-alkylthiomethyl-4-hydroxy-pyrimidines thus obtained with an oxidizing agent, for example hydrogen peroxide or m-chloroperbenzoic acid, at temperatures between 0° and 40° C., if appropriate using a diluent, for example acetic acid or chloroform.

Examples of the 4-hydroxy-pyrimidines of the formula (II) which may be mentioned are: 2-methylsulphinylmethyl-, 2-ethylsulphinylmethyl-, 2-n-propylsulphinylmethyl-, 2-iso-propylsulphinylmethyl-, 2-methylsulphonylmethyl-, 2-ethylsulphonylmethyl-, 2-n-propylsulphonylmethyl- and 2-iso-propylsulphonylmethyl-4-hydroxy-pyrimidine, 2-methylsulphinylmethyl-, 2-ethylsulphinyl-methyl-, 2-n-propylsulphinylmethyl-, 2-iso-propylsulphinylmethyl-, 2-methylsulphonylmethyl-, 2-ethylsulphonylmethyl-, 2-n-propylsulphonylmethyl- and 2-iso-propylsulphonylmethyl-5-methyl-4-hydroxy-pyrimidine, 2-methylsulphinylmethyl-, 2-ethylsulphinylmethyl-, 2-n-propylsulphinylmethyl-, 2-iso-propylsulphinylmethyl-, 2-methylsulphonylmethyl-, 2-ethylsulphonylmethyl-, 2-n-propylsulphonylmethyl- and 2-iso-propylsulphonylmethyl-5-ethyl-4-hydroxy-pyrimidine, 2-methylsulphinylmethyl-, 2-ethylsulphinylmethyl-, 2-n-propylsulphinylmethyl-, 2-iso-propylsulphinylmethyl-, 2-methylsulphonylmethyl-, 2-ethylsulphonylmethyl-, 2-n-propylsulphonylmethyl- and 2-iso-propylsulphonylmethyl-5-iso-propyl-4-hydroxy-pyrimidine, 2-methylsulphinylmethyl-, 2-ethylsulphinylmethyl-, 2-n-propylsulphinylmethyl-, 2-iso-propylsulphinylmethyl-, 2-methylsulphonylmethyl-, 2-ethylsulphonylmethyl-, 2-n-propylsulphonylmethyl- and 2-iso-propylsulphonylmethyl-6-methyl-4-hydroxy-pyrimidine, 2-methylsulphinylmethyl-, 2-ethylsulphinylmethyl-, 2-n-propylsulphinylmethyl-, 2-iso-propylsulphinylmethyl-, 2-methylsulphonylmethyl-, 2-ethylsulphonylmethyl-, 2-n-propylsulphonylmethyl- and 2-iso-propylsulphonylmethyl-5,6-dimethyl-4-hydroxy-pyrimidine, 2-methylsulphinylmethyl-, 2-ethylsulphinylmethyl-, 2-n-propylsulphinylmethyl-, 2-iso-propylsulphinylmethyl-, 2-methylsulphonylmethyl-, 2-ethylsulphonylmethyl-, 2-n-propylsulphonylmethyl- and 2-iso-propylsulphonylmethyl-5-ethyl-6-methyl-4-hydroxy-pyrimidine, 2-methylsulphinylmethyl-, 2-ethylsulphinylmethyl-, 2-n-propylsulphinylmethyl-, 2-iso-propylsulphinylmethyl-, 2-methylsulphonylmethyl-, 2-ethylsulphonylmethyl-, 2-n-propylsulphonylmethyl- and 2-iso-propylsulphonylmethyl-5-n-propyl-6-methyl-4-hydroxy-pyrimidine, 2-methylsulphinylmethyl-, 2-ethylsulphinylmethyl-, 2-n-propylsulphinylmethyl-, 2-iso-propylsulphinylmethyl-, 2-methylsulphonylmethyl-, 2-ethylsulphonylmethyl-, 2-n-propylsulphonylmethyl- and 2-iso-propylsulphonylmethyl-5-iso-propyl-6-methyl-4-hydroxy-pyrimidine, 2-methylsulphinylmethyl-, 2-ethylsulphinylmethyl-, 2-n-propylsulphinylmethyl-, 2-iso-propylsulphinylmethyl-, 2-methylsulphonylmethyl-, 2-ethylsulphonylmethyl-, 2-n-propylsulphonylmethyl- and 2-iso-propylsulphonylmethyl-5-n-butyl-6-methyl-4-hydroxy-pyrimidine, 2-methylsulphinylmethyl-, 2-ethylsulphinylmethyl-, 2-n-propylsulphinylmethyl-, 2-iso-propylsulphinylmethyl-, 2-methylsulphonylmethyl-, 2-ethylsulphonylmethyl-, 2-n-propylsulphonylmethyl- and 2-iso-propylsulphonylmethyl-5-methyl-6-tert.-butyl-4-hydroxy-pyrimidine, 2-methylsulphinylmethyl-, 2-ethylsulphinylmethyl-, 2-n-propylsulphinylmethyl-, 2-iso-propylsulphinylmethyl-, 2-methylsulphonylmethyl-, 2-ethylsulphonylmethyl-, 2-n-propylsulphonylmethyl- and 2-iso-propylsulphonylmethyl-5-chloro-6-methyl-4-hydroxy-pyrimidine, 2-methylsulphinylmethyl-, 2-ethylsulphinylmethyl-, 2-n-propylsulphinylmethyl-, 2-iso-propylsulphinylmethyl-, 2-methylsulphonylmethyl-, 2-ethylsulphonylmethyl-, 2-n-propylsulphonylmethyl- and 2-iso-propylsulphonylmethyl-5-bromo-6-methyl-4-hydroxy-pyrimidine, 2-methylsulphinylmethyl-, 2-ethylsulphinylmethyl-, 2-n-propylsulphinylmethyl-, 2-iso-propylsulphinylmethyl-, 2-methylsulphonylmethyl-, 2-ethylsulphonylmethyl-, 2-n-propylsulphonylmethyl- and 2-iso-propylsulphonylmethyl-5,6-trimethylene-4-hydroxy-pyrimidine and 2-methylsulphinylmethyl-, 2-ethylsulphinylmethyl-, 2-n-propylsulphinylmethyl-, 2-iso-propylsulphinylmethyl-, 2-methylsulphonylmethyl-, 2-ethylsulphonylmethyl-, 2-n-propylsulphonylmethyl- and 2-iso-propylsulphonylmethyl-5,6-tetramethylene-4-hydroxy-pyrimidine.

N,N-Dimethyl-carbamic acid chloride may be mentioned as an example of the carbamic acid halides of the formula (III) to be used in process variant (a). This compound has been known for a long time, as have the reactants phosgene and dimethylamine to be employed in process variant (b).

The formula (I) provides a definition of the N,N-dimethyl-carbamic acid O-pyrimidin-4-yl esters to be used as starting compounds in process variants (c) and (d), with the proviso that n represents zero.

Preferably, in this formula, R, $R^1$ and $R^2$ have those meanings which have already been mentioned as preferred in the case of the definition of R, $R^1$ and $R^2$ in formula (I), with the proviso that n represents 1 or 2. The starting compounds of the formula (I) in which n represents zero are obtained by a process analogous to process variant (a), for example by reacting the corresponding 2-alkylthio-methyl-4-hydroxypyrimidines of the formula (II) in which n represents zero with N,N-dimethyl-carbamic acid chloride at temperatures between 20° and 100° C., if appropriate in the presence of an acid acceptor, for example potassium carbonate, and if appropriate using a diluent, for example acetonitrile, and working up the product by filtering the reaction mixture and stripping off the diluent from the filtrate.

Examples which may be mentioned of starting compounds of the formula (I) in which n represents zero are: N,N-dimethyl-carbamic acid O-(2-methylthiomethyl-pyrimidin-4-yl), O-(2-ethylthiomethyl-pyrimidin-4-yl), O-(2-n-propylthiomethyl-pyrimidin-4-yl), O-(2-iso-propylthiomethyl-pyrimidin-4-yl), O-(2-methylthiomethyl-5-methyl-pyrimidin-4-yl), O-(2-ethylthiomethyl-5-methyl-pyrimidin-4-yl), O-(2-n-propylthiomethyl-5-methyl-pyrimidin-4-yl), O-(2-iso-propylthiomethyl-5-methyl-pyrimidin-4-yl), O-(2-methylthiomethyl-5-ethyl-pyrimidin-4-yl), O-(2-ethylthiomethyl-5-ethyl-pyrimidin-4-yl), O-(2-n-propylthiomethyl-5-ethyl-pyrimidin-4-yl), O-(2-iso-propylthiomethyl-5-ethyl-pyrimidin-4-yl), O-(2-methylthiomethyl-5-iso-propyl-pyrimidin-4-yl), O-(2-ethylthiomethyl-5-iso-propyl-pyrimidin-4-yl), O-(2-n-propylthiomethyl-5-iso-propyl-pyrimidin-4-yl), O-(2-iso-propylthiomethyl-5-iso-propyl-pyrimidin-4-yl), O-(2-methylthiomethyl-6-methyl-pyrimidin-4-yl), O-(2-ethylthiomethyl-6-methyl-pyrimidin-4-yl), O-(2-n-propylthiomethyl-6-methyl-pyrimidin-4-yl), O-(2-iso-propylthiomethyl-6-methyl-pyrimidin-4-yl), O-(2-methylthiomethyl-5,6-dimethyl-pyrimidin-4-yl), O-(2-ethylthiomethyl-5,6-dimethyl-pyrimidin-4-yl), O-(2-n-propylthiomethyl-5,6-dimethyl-pyrimidin-4-yl), O-(2-iso-propylthiomethyl-5,6-dimethyl-pyrimidin-4-yl), O-(2-methylthiomethyl-5-ethyl-6-methyl-pyrimidin-4-yl), O-(2-ethylthiomethyl-5-ethyl-6-methyl-pyrimidin-4-yl), O-(2-n-propylthiomethyl-5-ethyl-6-methyl-pyrimidin-4-yl), O-(2-iso-propylthiomethyl-5-ethyl-6-methyl-pyrimidin-4-yl), O-(2-methylthiomethyl-5-n-propyl-6-methyl-pyrimidin-4-yl), O-(2-ethylthiomethyl-5-n-propyl-6-methyl-pyrimidin-4-yl), O-(2-n-propylthiomethyl-5-n-propyl-6-methyl-pyrimidin-4-yl), O-(2-iso-propylthiomethyl-5-n-propyl-6-methyl-pyrimidin-4-yl)-, O-(2-methylthiomethyl)-5-iso-propyl-6-methyl-pyrimidin-4-yl), O-(2-ethylthiomethyl-5-iso-propyl-6-methyl-pyrimidin-4-yl), O-(2-n-propylthiomethyl-5-iso-propyl-6-methyl-pyrimidin-4-yl), O-(2-iso-propylthiomethyl-5-iso-propyl-6-methyl-pyrimidin-4-yl), O-(2-methylthiomethyl-5-n-butyl-6-methyl-pyrimidin-4-yl), O-(2-ethylthiomethyl-5-n-butyl-6-methyl-pyrimidin-4-yl), O-(2-n-propylthiomethyl-5n-butyl-6-methyl-pyrimidin-4-yl), O-(2-iso-propylthiomethyl-5-n-butyl-6-methyl-pyrimidin-4-yl), O-(2-methylthiomethyl-6-tert.-butyl-5-methyl-pyrimidin-4-yl), O-(2-ethylthiomethyl-6-tert.-butyl-5-methyl-pyrimidin-4-yl), O-(2-n-propylthiomethyl-6-tert.-butyl-5-methyl-pyrimidin-4-yl), O-(2-iso-propylthiomethyl-6-tert.-butyl-5-methyl-pyrimidin-4-yl), O-(2-methylthiomethyl-5-chloro-6-methyl-pyrimidin-4-yl), O-(2-ethylthiomethyl-5-chloro-6-methyl-pyrimidin-4-yl), O-(2-n-propylthiomethyl-5-chloro-6-methyl-pyrimidin-4-yl), O-(2-iso-propylthiomethyl-5-chloro-6-methyl-pyrimidin-4-yl), O-(2-methylthiomethyl-5-bromo-6-methyl-pyrimidin-4-yl), O-(2-ethylthiomethyl-5-bromo-6-methyl-pyrimidin-4-yl), O-(2-n-propylthiomethyl-5-bromo-6-methyl-pyrimidin-4-yl), O-(2-iso-propylthiomethyl-5-bromo-6-methyl-pyrimidin-4-yl), O-(2-methylthiomethyl-5,6-trimethylene-pyrimidin-4-yl), O-(2-ethylthiomethyl-5,6-trimethylene-pyrimidin-4-yl), O-(2-n-propylthiomethyl-5,6-trimethylene-pyrimidin-4-yl), O-(2-iso-propylthiomethyl-5,6-trimethylene-pyrimidin-4-yl), O-(2-methylthiomethyl-5,6-tetramethylene-pyrimidin-4-yl), O-(2-ethylthiomethyl-5,6-tetramethylene-pyrimidin-4-yl), O-(2-n-propylthiomethyl-5,6-tetramethylene-pyrimidin-4-yl) and O-(2-iso-propylthiomethyl-5,6-tetramethylene-pyrimidin-4-yl) esters.

The oxidizing agents hydrogen peroxide and m-chloroperbenzoic acid to be used in process variants (c) and (d) respectively are known compounds.

In general, process variants (a) to (d) for the preparation of the new N,N-dimethyl-carbamic acid O-pyrimidinyl esters are carried out using diluents. Possible diluents are virtually any of the inert organic solvents. These include, in particular, aliphatic and aromatic, optionally chlorinated hydrocarbons, such as benzine, benzene, toluene, xylene, methylene chloride, chloroform, carbon tetrachloride, chlorobenzene and o-dichlorobenzene; ethers, such as diethyl ether, dibutyl ether, tetrahydrofuran and dioxane; ketones, such as acetone, methyl ethyl ketone, methyl isopropyl ketone and methyl isobutyl ketone; and nitriles, such as acetonitrile and propionitrile.

Process variant (c) can advantageously be carried out using aliphatic carboxylic acids as diluents, for example formic acid, acetic acid or propionic acid.

In general, process variants (a) and (b) are carried out using an acid acceptor. Acid acceptors which can be used are any of the customary acid-binding agents. Alkali metal carbonates and alcoholates, such as sodium carbonate and potassium carbonate, sodium methylate or ethylate and potassium methylate or ethylate, and furthermore aliphatic, aromatic or heterocyclic amines, for example triethylamine, trimethylamine, dimethylaniline, dimethylbenzylamine and pyridine, have proved particularly suitable.

The process variants according to the invention are in general carried out at temperatures of from 0° to 150° C. The temperature range of from 20° to 100° C. is preferred for process variant (a) and the range of from 0° to 50° C. is preferred for process variants (b), (c) and (d). In general, the reactions are carried out under normal pressure.

For carrying out process variants (a) and (b), between 1.0 and 1.3, preferably between 1.0 and 1.15, mols of N,N-dimethyl-carbamic acid chloride or, respectively, phosgene and dimethylamine are employed per mol of 4-hydroxy-pyrimidine of the formula (II). In general, the reaction is carried out in a diluent in the presence of an acid acceptor. When the reaction has ended, the mixture is filtered and the solvent is distilled off from the filtrate in vacuo.

The reactants are preferably employed in equimolar amounts in process variant (c). If water-miscible diluents are used, these are distilled off in vacuo after the end of the reaction. The residue is then dissolved in a water-immiscible solvent, for example methylene chloride, and the product is worked up by customary methods, for example by washing, drying and filtering the solution and distilling off the solvent from the filtrate.

The m-chloro-perbenzoic acid used as the oxidizing agent in process variant (d) is usually employed in excess, and in particular between 2 and 3 mols are used per mol of N,N-dimethyl-carbamic acid O-(2-alkylthiomethyl-pyrimidin-4-yl) ester. In general, the reaction is carried out in a water-immiscible solvent. When the reaction has ended, the mixture is washed until neutral, dried and filtered and the solvent is distilled off from the filtrate in vacuo.

The new compounds are obtained in the form of oils, some of which cannot be distilled without decomposition, but which can be freed from the last volatile constituents by so-called "incipient distillation", that is by prolonged heating to moderately elevated temperatures under reduced pressure, and can be purified in this manner. The refractive index is used for their characterization.

If the new compounds are obtained in the solid form after distilling off the solvent, they are purified by recrystallization. The melting point is then used for their characterization.

The N,N-dimethyl-carbamic acid O-pyrimidinyl esters according to the invention are distinguished by a high insecticidal activity, in particular also a root-systemic activity, and a fungicidal activity.

Fungicidal agents are employed in plant protection for combating Plasmodiophoromycetes, Oomycetes, Chtridiomycetes, Zygomycetes, Ascomycetes, Basidiomycetes and Deuteromycetes.

The active compounds are well tolerated by plants, have a favorable level of toxicity to warm-blooded animals, and can be used for combating arthropod pests, especially insects, which are encountered in agriculture, in forestry, in the protection of stored products and of materials, and in the hygiene field. They are active against normally sensitive and resistant species and against all or some stages of development. The above-mentioned pests include:

from the class of the Isopoda, for example *Oniscus asellus, Armadillidium vulgare* and *Porcellio scaber;* from the class of the Diplopoda, for example *Blaniulus guttulatus;* from the class of the Chilopoda, for example *Geophilus carpophagus* and Scutigera spec.;

from the class of the Symphyla, for example *Scutigerella immaculata;* from the order of the Thysanura, for example *Lepisma saccharina;* from the order of the Collembola, for example *Onychiurus armatus;* from the order of the Orthoptera, for example *Blatta orientalis, Periplaneta americana, Leucophaea maderae, Blattella germanica, Acheta domesticus,* Gryllotalpa spp., *Locusta migratoria migratorioides, Melanoplus differentialis* and *Schistocerca gregaria;* from the order of the Dermaptera, for example *Forficula auricularia;* from the order of the Isoptera, for example Reticulitermes spp.;

from the order of the Anoplura, for example *Phylloxera vastatrix,* Pemphigus spp., *Pediculus humanus corporis,* Haematopinus spp. and Linognathus spp.;

from the order of the Mallophaga, for example Trichodectes spp. and Damalinea spp.;

from the order of the Thysanoptera, for example *Hercinothrips femoralis* and *Thrips tabaci;* from the order of the Heteroptera, for example Eurygaster spp., *Dysdercus intermedius, Piesma quadrata, Cimex lectularius, Rhodnius prolixus* and Triatoma spp.;

from the order of the Homoptera, for example *Aleurodes brassicae, Bemisia tabaci, Trialeurodes vaporariorum, Aphis gossypii, Brevicoryne brassicae, Cryptomyzus ribis, Doralis fabae, Doralis pomi, Eriosoma lanigerum, Hyalopterus arundinis, Macrosiphum avenae,* Myzus spp., *Phorodon humuli, Rhopalosiphum padi,* Empoasca spp., *Euscelis bilobatus, Nephotettix cincticeps, Lecanium corni, Saissetia oleae, Laodelphax striatellus, Nilaparvata lugens, Aonidiella aurantii, Aspidiotus hederae,* Pseudoccus spp. and Psylla spp.;

from the order of the Lepidoptera, for example *Pectinophora gossypiella, Bupalus piniarius, Cheimatobia brumata, Lithocolletis blancardella, Hyponomeuta padella, Plutella maculipennis, Malacosoma neustria, Euproctis chrysorrhoea,* Lymantria spp., *Bucculatrix thurberiella, Phyllocnistis citrella,* Agrotis spp., Euxoa spp., Feltia spp., *Earias insulana,* Heliothis spp., *Laphygma exigua, Mamestra brassicae, Panolis flammea, Prodenia litura,* Spodoptera spp., *Trichoplusia ni, Carpocapsa pomonella,* Pieris spp., Chilo spp., *Pyrausta nubilalis, Ephestia keuhniella, Galleria mellonella, Cacoecia podana, Capua reticulana, Choristoneura fumiferana, Clysia ambiguella, Homona magnanima* and *Tortrix viridana;* from the order of the Coleoptera, for example *Anobium punctatum, Rhizopertha dominica, Bruchidius obtectus, Acanthoscelides obtectus, Hylotrupes bajulus, Agelastica alni, Leptinotarsa decemlineata, Phaedon cochleariae,* Diabrotica spp., *Psylliodes chrysocephala, Epilachna varivestis,* Atomaria spp., *Oryzaephilus surinamenis,* Anthonomus· spp., Sitophilus spp., *Otiorrhynchus sulcatus, Cosmopolites sordidus, Ceuthorrhynchus assimilis, Hypera postica,* Dermestes spp., Trogoderma spp., Anthrenus spp., Attagenus spp., Lyctus spp., *Meligethes aeneus,* Ptinus spp., *Niptus hololeucus, Gibbium psylloides,* Tribolium spp., *Tenebrio molitor,* Agriotes spp., Conoderus spp., *Melolontha melolontha, Amphimallon solstitialis* and *Costelytra zealandica;* from the order of the Hymenoptera, for example Diprion spp., Hoplocampa spp., Lasius spp., *Monomorium pharaonis* and Vespa spp.;

from the order of the Diptera, for example Aedes spp., Anopheles spp., Culex spp., *Drosophila melanogaster,* Musca spp., Fannia spp., *Calliphora erythrocephala,* Lucilia spp., Chrysomyia spp., Cuterebra spp., Gastrophilus spp., Hyppobosca spp., Stomoxys spp., Oestrus spp., Hypoderma spp., Tabanus spp., Tannia spp., *Bibio hortulanus, Oscinella frit,* Phorbia spp., *Pegomyia hyoscyami, Ceratitis capitata, Dacus oleae* and *Tipula paludosa;* from the order of the Siphonaptera, for example *Xenopsylla cheopis* and Ceratophyllus spp..

The active compounds can be converted into the customary formulations, such as solutions, emulsions, wettable powders, suspensions, powders, dusting agents, foams, pastes, soluble powders, granules, aerosols, suspension-emulsion concentrates, seed-treatment powders, natural and synthetic materials impregnated with active compound, very fine capsules in polymeric substances, coating compositions for use on seed, and formulations used with burning equipment, such as fumigating cartridges, fumigating cans and fumigating coils, as well as ULV cold mist and warm mist formulations.

These formulations may be produced in known manner, for example by mixing the active compounds with extenders, that is to say liquid or liquefied gaseous or solid diluents or carriers, optionally with the use of surface-active agents, that is to say emulsifying agents and/or dispersing agents and/or foam-forming agents. In the case of the use of water as an extender, organic solvents can, for example, also be used as auxiliary solvents.

As liquid diluents or carriers, especially solvents, there are suitable in the main, aromatic hydrocarbons, such as xylene, toluene or alkyl naphthalenes, chlorinated aromatic or chlorinated aliphatic hydrocarbons, such as chlorobenzenes, chloroethylenes or methylene chloride, aliphatic or alicyclic hydrocarbons, such as cyclohexane or paraffins, for example mineral oil fractions, alcohols, such as butanol or glycol as well as their ethers and esters, ketones, such as acetone, methyl ethyl ketone, methyl isobutyl ketone or cyclohexanone, or strongly polar solvents, such as dimethylformamide and dimethylsulphoxide, as well as water.

By liquefied gaseous diluents or carriers are meant liquids which would be gaseous at normal temperature and under normal pressure, for example aerosol propellants, such as halogenated hydrocarbons as well as butane, propane, nitrogen and carbon dioxide.

As solid carriers there may be used ground natural minerals, such as kaolins, clays, talc, chalk, quartz, attapulgite, montmorillonite or diatomaceous earth, and ground synthetic minerals, such as highly-dispersed silicic acid, alumina and silicates. As solid carriers for granules there may be used crushed and fractionated natural rocks such as calcite, marble, pumice, sepiolite and dolomite, as well as synthetic granules of inorganic and organic meals, and granules of organic material such as sawdust, coconut shells, corn cobs and tobacco stalks.

As emulsifying and/or foam-forming agents there may be used non-ionic and anionic emulsifiers, such as polyoxyethylene-fatty acid esters, polyoxyethylene-fatty alcohol ethers, for example alkylaryl polyglycol ethers, alkyl sulphonates, alkyl sulphates, aryl sulphonates as well as albumin hydrolysis products. Dispersing agents include, for example, lignin sulphite waste liquors and methylcellulose.

Adhesives such as carboxymethylcellulose and natural and synthetic polymers in the form of powders, granules or latices, such as gum arabic, polyvinyl alcohol and polyvinyl acetate, can be used in the formulations.

It is possible to use colorants such as inorganic pigments, for example iron oxide, titanium oxide and Prussian Blue, and organic dyestuffs, such as alizarin dyestuffs, azo dyestuffs or metal phthalocyanine dyestuffs, and trace nutrients, such as salts of iron, manganese, boron, copper, cobalt, molybdenum and zinc.

The formulations in general contain from 0.1 to 95 percent by weight of active compound, preferably from 0.5 to 90 percent by weight.

The active compounds according to the invention may be used in the form of their formulations of the types that are commercially available or in the use forms prepared from these formulations.

The active compound content of the use forms prepared from the formulations of the types that are commercially available can vary within wide ranges. The active compound concentration of the use forms can be from 0.0000001 to 100% by weight of active compound, preferably from 0.01 to 10% by weight.

The compounds may be employed in a customary manner appropriate for the particular use forms.

The present invention also provides an arthropodicidal or fungicidal composition containing as active ingredient a compound of the present invention in admixture with a solid or liquefied gaseous diluent or carrier or in admixture with a liquid diluent or carrier containing a surface-active agent.

The present invention also provides a method of combating arthropods (especially insects) or fungi which comprises applying to the arthropods or fungi, or to a habitat thereof, a compound of the present invention alone or in the form of a composition containing as active ingredient a compound of the present invention in admixture with a diluent or carrier.

The present invention further provides crops protected from damage by arthropods or fungi by being grown in areas in which immediately prior to and/or during the time of the growing a compound of the present invention was applied alone or in admixture with a diluent or carrier.

It will be seen that the usual methods of providing a harvested crop may be improved by the present invention.

The preparation of the novel compounds is shown in the following illustrative examples:

EXAMPLE 1

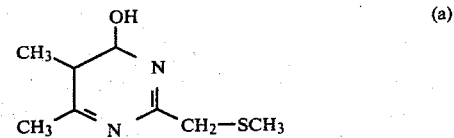
(a)

A mixture of 129 g (0.75 mol) of 2-chloromethyl-5,6-dimethyl-4-hydroxy-pyrimidine, 52.5 g (0.75 mol) of sodium methylmercaptide and 700 ml of acetonitrile was heated to the boil under reflux for 3 hours. The hot reaction mixture was filtered and the filtrate was evaporated to dryness in vacuo. 45.5 g (33% of theory) of 2-methylthiomethyl-5,6-dimethyl-4-hydroxy-pyrimidine were obtained in the form of a beige powder with a melting point of 142° C.

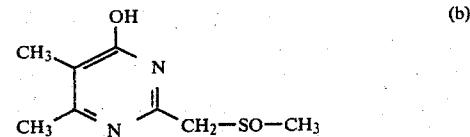
(b)

6.8 g (0.1 mol) of 50% strength hydrogen peroxide were added to a mixture of 18.4 g (0.1 mol) of 2-methylthiomethyl-4-hydroxy-5,6-dimethylpyrimidine in 100 ml of glacial acetic acid at 10° C. The mixture was subsequently stirred for 3 hours, without cooling, about 300 ml of ether were added and the product which had precipitated was filtered off. 17 g (85% of theory) of 2-methysulphinylmethyl-4-hydroxy-5,6-dimethyl-pyrimidine were thus obtained in the form of a grey powder with a melting point of 112° C.

(c) 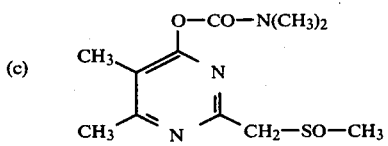 (1)

A mixture of 20 g (0.1 mol) of 2-methylsulphinyl-methyl-4-hydroxy-5,6-dimethylpyrimidine, 20.7 g (0.15 mol) of potassium carbonate, 200 ml of acetonitrile and 11.8 g (0.11 mol) of N,N-dimethylcarbamic acid chloride was boiled under reflux for 18 hours. After cooling to room temperature, the reaction mixture was filtered and the filtrate was then evaporated in vacuo. 21.3 g (78% of theory) of N,N-dimethyl-carbamic acid O-(2-methylsulphinylmethyl-5,6-dimethyl-pyrimidin-4-yl) ester remained in the form of beige crystals with a melting point of 104° C.

EXAMPLE 2

(a) 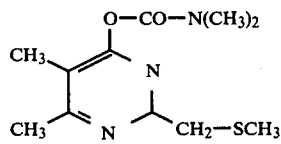

A mixture of 18.5 g (0.1 mol) of 2-methylthiomethyl-5,6-dimethyl-4-hydroxy-pyrimidine, 20.7 g (0.15 mol) of potassium carbonate, 11.8 g (0.11 mol) of N,N-dimethyl-carbamic acid chloride and 200 ml of acetonitrile was heated to the boil under reflux for 12 hours. After cooling to room temperature, the reaction mixture was filtered and the filtrate was evaporated in vacuo. 19.1 g (75% of theory) of N,N-dimethyl-carbamic acid O-(2-methylthiomethyl-5,6-dimethyl-pyrimidin-4-yl) ester remained in the form of a brown oil with the refractive index $n_D^{23}$: 1.5491.

(b) 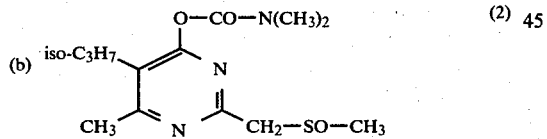 (2)

3.4 g (0.05 mol) of 50% strength hydrogen peroxide were added to a solution of 14.2 g (0.05 mol) of N,N-dimethyl-carbamic acid O-(2-methylthiomethyl-5-iso-propyl-6-methyl-pyrimidin-4-yl) ester in 50 ml of glacial acetic acid at 5°–10° C. The mixture was subsequently stirred at room temperature for 6 hours and the solvent was then distilled off in vacuo. The residue was dissolved in 100 ml of methylene chloride and the methylene chloride solution was washed with a solution of 10 g of potassium carbonate in 15 ml of water. The organic phase was separated off and dried over sodium sulphate. The solvent was then distilled off in vacuo. 11 g (74% of theory) of N,N-dimethyl-carbamic acid O-(2-methylsulphinylmethyl-5-iso-propyl-6-methyl-pyrimidin-4-yl) ester were thus obtained in the form of beige crystals with a melting point of 80° C.

EXAMPLE 3

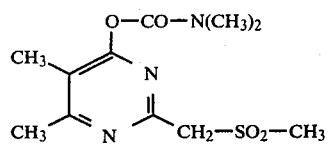 (3)

A solution of 31.2 g of m-chloroperbenzoic acid in 250 ml of chloroform was added dropwise to a solution of 17.9 g (0.07 mol) of N,N-dimethyl-carbamic acid O-(2-methyl-thiomethyl-5,6-dimethyl-pyrimidin-4-yl) ester in 50 ml of chloroform at 5° C. The mixture was subsequently stirred overnight at room temperature and then filtered. The filtrate was washed with 10 ml of concentrated potassium carbonate solution and dried over sodium sulphate. The solvent was then stripped off in vacuo. 17 g (85% of theory) of N,N-dimethyl-carbamic acid O-(2-methylsulphonylmethyl-5,6-dimethyl-pyrimidin-4-yl) ester remained in the form of beige crystals with a melting point of 122° C.

The following compounds of the formula

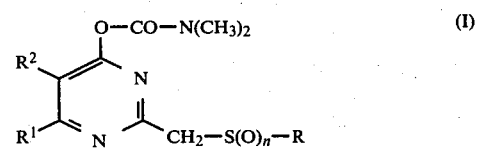 (I)

could be prepared analogously to one of Examples 1 to 3:

| Compound No. | R | R¹ | R² | n | Yield (% of theory) | Physical data (Refractive index: melting point °C.) |
|---|---|---|---|---|---|---|
| 4 | CH₃ | CH₂—CH₂—CH₂ | | 2 | 72 | 109 |
| 5 | CH₃ | CH₃ | C₃H₇-iso | 2 | 70 | 142 |
| 6 | CH₃ | CH₃ | C₄H₉-n | 2 | 61 | 76 |
| 7 | CH₃ | CH₂—CH₂—CH₂—CH₂ | | 1 | 84 | 134 |
| 8 | CH₃ | CH₃ | C₄H₉-n | 1 | 96 | $n_D^{20}$:1.4557 |
| 9 | CH₃ | CH₂—CH₂—CH₂ | | 1 | 61 | 115 |
| 10 | CH₃ | CH₂—CH₂—CH₂—CH₂ | | 2 | 77 | 130 |
| 11 | C₂H₅ | CH₃ | H | 1 | | |
| 12 | C₂H₅ | CH₃ | CH₃ | 1 | 66 | |
| 13 | C₂H₅ | CH₃ | H | 2 | | |
| 14 | C₂H₅ | CH₃ | CH₃ | 2 | 40 | |
| 15 | CH₃ | CH₃ | C₂H₅ | 1 | 91 | $n_D^{21}$:1.5351 |
| 16 | CH₃ | CH₃ | C₂H₅ | 2 | 66 | 88 |
| 17 | CH₃ | CH₃ | C₃H₇-n | 1 | 94 | $n_D^{21}$:1.5293 |
| 18 | CH₃ | CH₃ | C₃H₇-n | 2 | 83 | 103 |
| 19 | C₂H₅ | CH₂—CH₂—CH₂ | | 1 | | |
| 20 | C₂H₅ | CH₂—CH₂—CH₂ | | 2 | 89 | $n_D^{25}$:1.5311 |
| 21 | C₃H₇-n | CH₂—CH₂—CH₂ | | 1 | | |
| 22 | C₃H₇-n | CH₂—CH₂—CH₂ | | 2 | | |
| 23 | CH₃ | H | CH₃ | 1 | | |
| 24 | CH₃ | H | CH₃ | 2 | | |
| 25 | CH₃ | H | C₃H₇-iso | 1 | | |
| 26 | CH₃ | H | C₃H₇-iso | 2 | | |
| 27 | CH₃ | H | H | 1 | | |
| 28 | CH₃ | H | H | 2 | | |
| 29 | CH₃ | CH₃ | H | 1 | | |
| 30 | CH₃ | CH₃ | H | 2 | | |
| 31 | C₂H₅ | H | C₃H₇-iso | 1 | | |
| 32 | C₂H₅ | H | C₃H₇-iso | 2 | | |
| 33 | CH₃ | H | C₂H₅ | 1 | | |
| 34 | CH₃ | H | C₂H₅ | 2 | | |
| 35 | CH₃ | CH₃ | Br | 1 | | |
| 36 | CH₃ | CH₃ | Br | 2 | | |

-continued

| Compound No. | R | R¹ | R² | n | Yield (% of theory) | Physical data (Refractive index: melting point °C.) |
|---|---|---|---|---|---|---|
| 37 | CH₃ | CH₃ | Cl | 1 | | |
| 38 | CH₃ | CH₃ | Cl | 2 | | |
| 39 | CH₃ | C₄H₉-tert. | CH₃ | 1 | | |
| 40 | CH₃ | C₄H₉-tert. | CH₃ | 2 | | |

The pesticidal activity of the compounds of this invention is illustrated by the following examples wherein the compounds according to the present invention are each identified by the number (given in brackets) from preparative Examples 1 to 3:

EXAMPLE 4

Myzus test

Solvent: 3 parts by weight of dimethylformamide
Emulsifier: 1 part by weight of alkylaryl polyglycol ether To produce a suitable preparation of active compound, 1 part by weight of the active compound was mixed with the stated amount of solvent containing the stated amount of emulsifier and the concentrate was diluted with water to the desired concentration.

Cabbage plants (*Brassica oleracea*) which had been heavily infested with peach aphids (*Myzus persicae*) were treated by being dipped into the preparation of active compound of the desired concentration.

After the specified periods of time, the degree of destruction was determined as a percentage: 100% meant that all of the aphids were killed whereas 0% meant that none of the aphids were killed.

In this test, for example, the following compounds showed a superior activity compared with the prior art: (1), (3), (2), (5), (8), (6), (9), (4), (7) and (10).

EXAMPLE 5

Critical concentration test/root-systemic action

Test animal: *Myzus persicae*
Solvent: 3 parts by weight of acetone
Emulsifier: 1 part by weight of alkylaryl polyglycol ether To produce a suitable preparation of active compound, 1 part by weight of active compound was mixed with the stated amount of solvent, the stated amount of emulsifier was added and the concentrate was diluted with water to the desired concentration.

The preparation of active compound was intimately mixed with the soil. The concentration of the active compound in the preparation was of practically no importance; only the amount of active compound per unit volume of soil, which is given hereinafter in ppm (=mg/l), was decisive. The treated soil was filled into pots and these were planted with cabbage (*Brassica oleracea*). The active compound could in this way be taken up from the soil by the plant roots and be transported into the leaves.

To demonstrate the root-systemic effect, only the leaves were infested with the above-mentioned test animals after 7 days. After a further 2 days, the results were evaluated by counting or estimating the dead insects. The root-systemic action of the active compound was deduced from the destruction data. It was 100% when all of the test insects had been killed and 0% when just as many test insects were still alive as in the case of the untreated control.

In this test, for example, the following compounds showed a superior action compared to the prior art: (10), (4), (5), (6), (2), (8), (9), (3).

EXAMPLE 6

Shoot treatment test/cereal rust (leaf-destructive mycosis)/protective

To produce a suitable preparation of active compound, 0.25 part by weight of active compound was taken up in 25 parts by weight of dimethylformamide and 0.06 part by weight of alkylaryl polyglycol ether and then 975 parts by weight of water were added. The concentrate was diluted with water to the desired final concentration of the spray liquor.

To test the protective activity, one-leaved young wheat plants of the Michigan Amber variety were inoculated with a uredospore suspension of *Puccinia recondita* in 0.1% strength aqueous agar. After the spore suspension had dried on, the wheat plants were sprayed with the preparation of active compound until dew-moist and were placed, for incubation, in a greenhouse for 24 hours at about 20 deg. C. and 100% relative atmospheric humidity.

After 10 days' dwell time of the plants at a temperature of 20 deg. C. and 80–90% atmospheric humidity, the occurrence of rust pustules on the plant was evaluated. The degree of infection was expressed as a percentage of the infection of the untreated control plants. 0% denoted no infection and 100% denoted the same degree of infection as in the case of the untreated control. The more active the compound, the lower was the degree of rust infection.

In this test, for example, the following compound showed a superior action compared to the prior art: (7).

It will be appreciated that the instant specification and examples are set forth by way of illustration and not limitation, and that various modifications and changes may be made without departing from the spirit and scope of the present invention.

We claim:

1. An N,N-dimethyl-carbamic acid O-(2-substituted-methyl-pyrimidin-4-yl) ester of the formula

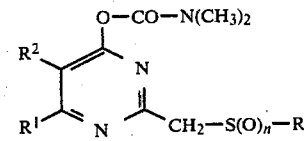

in which
R is alkyl with 1 to 5 carbon atoms,
R¹ is hydrogen or alkyl with 1 to 6 carbon atoms,
R² is hydrogen, alkyl with 1 to 6 carbon atoms or halogen, or
R¹ and R² together are alkylenyl with 3 to 5 carbon atoms, and
n is 1 or 2.

2. A compound according to claim 1, in which
R² is hydrogen, alkyl with 1 to 6 carbon atoms, chlorine or bromine, or
R¹ and R² together with α, ω-alkylenyl with 3 to 5 carbon atoms.

3. A compound according to claim 1, in which said compound is N,N-dimethyl-carbamic acid O-(2-methyl-sulphinylmethyl-5,6-dimethyl-pyrimidin-4-yl) ester of the formula

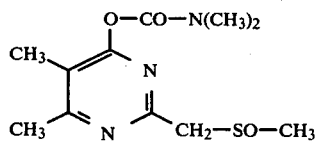

4. A compound according to claim 1, in which said compound is N,N-dimethyl-carbamic acid O-(2-methyl-sulphonylmethyl-5,6-dimethyl-pyrimidin-4-yl) ester of the formula

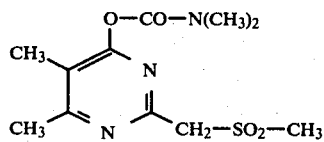

5. A compound according to claim 1, in which said compound is N,N-dimethyl-carbamic acid O-(2-methyl-sulphonylmethyl-5,6-trimethylene-pyrimidin-4-yl) ester of the formula

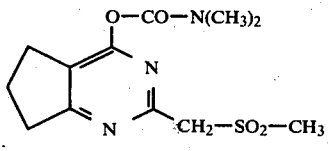

6. A compound according to claim 1, in which said compound is N,N-dimethyl-carbamic acid O-(2-methyl-sulphinylmethyl-5-6-trimethylene-pyrimidin-4-yl) ester of the formula

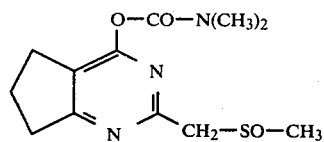

7. A compound according to claim 1, in which said compound is N,N-dimethyl-carbamic acid O-(2-methyl-sulphonylmethyl-5,6-tetramethylene-pyrimidin-4-yl) ester of the formula

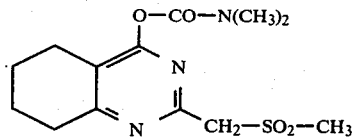

8. An arthropodicidal or fungicidal composition containing as active ingredient an arthropodicidally or fungicidally effective amount of a compound according to claim 1 in admixture with a diluent.

9. A method of combating arthropods or fungi which comprises applying to the arthropods or fungi, or to a habitat thereof, an arthropodicidally or fungicidally effective amount of a compound according to claim 1.

10. The method according to claim 9, in which said compound is
N,N-dimethyl-carbamic acid O-(2-methylsulphinyl-methyl-5,6-dimethyl-pyrimidin-4-yl) ester,
N,N-dimethyl-carbamic acid O-(2-methylsulphonyl-methyl-5,6-dimethyl-pyrimidin-4-yl) ester,
N,N-dimethyl-carbamic acid O-(2-methylsulphonyl-methyl-5,6-trimethylene-pyrimidin-4yl) ester,
N,N-dimethyl-carbamic acid O-(2-methylsulphinyl-methyl-5-6-trimethylene-pyrimidin-4-yl) ester, or
N,N-dimethyl-carbamic acid O-(2-methylsulphonyl-methyl-5-6-tetramethylene-pyrimidin-4-yl) ester.

* * * * *